United States Patent [19]

Budhu

[11] Patent Number: 4,854,175

[45] Date of Patent: Aug. 8, 1989

[54] SIMPLE SHEAR DEVICE FOR TESTING EARTHEN MATERIALS AND POWDERS

[75] Inventor: Muniram Budhu, Williamsville, N.Y.

[73] Assignee: The Research Foundation of State University of New York, Albany, N.Y.

[21] Appl. No.: 161,859

[22] Filed: Feb. 29, 1988

[51] Int. Cl.[4] ............................................. G01N 3/24
[52] U.S. Cl. ................................................... 73/841
[58] Field of Search .................. 73/841, 842, 844–846, 73/784, 794, 38

[56] References Cited

U.S. PATENT DOCUMENTS

| 2,498,198 | 2/1950 | Beeson | 73/38 |
|---|---|---|---|
| 2,705,418 | 4/1955 | Reichertz et al. | 73/38 |
| 3,353,407 | 11/1967 | Dietert et al. | 73/845 |
| 4,149,407 | 4/1979 | Strom et al. | 73/794 |
| 4,445,387 | 6/1984 | Hall et al. | 73/846 |

FOREIGN PATENT DOCUMENTS

| 0147238 | 8/1984 | Japan | 73/841 |
|---|---|---|---|
| 0100639 | 5/1986 | Japan | 73/841 |
| 0552540 | 4/1977 | U.S.S.R. | 73/842 |
| 0629284 | 10/1978 | U.S.S.R. | 73/846 |
| 0876835 | 10/1981 | U.S.S.R. | 73/841 |
| 0877410 | 10/1981 | U.S.S.R. | 73/842 |
| 0953085 | 8/1982 | U.S.S.R. | 73/784 |
| 0960376 | 9/1982 | U.S.S.R. | 73/841 |
| 0973702 | 11/1982 | U.S.S.R. | 73/784 |
| 1078274 | 3/1984 | U.S.S.R. | 73/841 |
| 1259142 | 9/1986 | U.S.S.R. | 73/841 |

OTHER PUBLICATIONS

Bjerrum et al., Direct Simple-Shear Tests on a Norwegian Quick Clay, Geotechnique 16, No. 1, pp. 1–20.
W. Kjellman, Testing the Shear Strength of Clay in Sweden, Geotechnique, vol. 2, No. 3, pp. 225–232.
Roscoe et al., An Apparatus for the Application of Simple Shear to Soil Samples, Proc. 3rd ICSMFE, vol. 1, 1953, pp. 186–191.
Ishibashi et al., Effect of Initial Shear on Cyclic Behavior of Sand, Journal of Geotechnical Engineering, vol. 11, No. 12, 1985, pp. 1395–1410.
Airey, Clays in Circular Simple Shear Apparatus, Ph.D. Thesis, Cambridge University, U.K., 1984.

*Primary Examiner*—Stewart J. Levy
*Assistant Examiner*—Robert R. Raevis
*Attorney, Agent, or Firm*—Michael L. Dunn

[57] ABSTRACT

A simple shear device and method for its use to test stress and strain characteristics of earthen samples and powders. The shear device particularly comprises a stacked plurality of plates which are slidably movable laterally relative to one another, which plates have a hollow central area for holding a cuboidal sample and spaced first and second platens having faces at between parallel and 45° relative orientation to one another, between which the plurality of plates containing the sample may be placed. A first force may be applied to the first platen urging it toward the second platen to compress the sample therebetween; a second force is applied to one of the platens to urge the platen in an angular direction relative to the direction of the first force to apply a shear force to the sample. The resulting stresses and strains in the sample are monitored when the forces are applied to the sample while confined between the platens.

26 Claims, 7 Drawing Sheets

SIMPLE SHEAR DEVICE FOR TESTING EARTHEN MATERIALS AND POWDERS

BACKGROUND OF THE INVENTION

The testing of earthen samples is a common practice to obtain accurate values pertaining to the strength and stability of the underlying materials under loading. In order to obtain accurate values it is necessary to test samples of materials under conditions simulating, as closely as possible, natural conditions. Several practical problems involving soils under or adjacent to embankments, cuttings, retaining walls, piles and offshore platforms involve soil behavior that can be closely simulated in the laboratory by subjecting a sample of soil or other earthen materials and powders to a simple shear test. There are several types of devices which can be used to test various characteristics of soils and other samples.

The present invention involves a type of device called the simple shear device. A simple shear device will test a sample of particulate geologic or mineralogic material under conditions of plane strain (a condition in which no strains occur in one of the Cartesian axes) with rotation of the principal axes of stress and strain. One of the advantages of a simple shear device is that it allows the principal axes of stresses and strains to rotate freely. A general soil element in the ground can expect to experience varying directions and magnitudes of principal stresses and it becomes important to study the behavior of soil samples in the laboratory under stress conditions in which rotation of principal axes can occur freely. In addition, simple shear devices distort as well as compress the sample. Shear can be simply defined as a straining action wherein tangentially applied forces produce a sliding or skewing type of deformation. Therefore, when shear is applied and distortion is allowed more accurate measurements are possible.

Analyses of soils and experiments in the simple shear devices showed that a region in the middle of the samples will be under uniform conditions of stresses and strains. However, instrumentation was not concentrated in this uniform region in routine simple shear devices. Rather the majority of simple shear results comes from measurements made over the plan area of the samples. These results, then, include apparatus effects of which the major one is stress concentrations. Thus, these results cannot be reliably used to describe the mechanical behavior of soils or other materials in simple shear.

Simple shear tests can be conducted on variations of 2 types of simple shear devices currently available; the Norwegian Geotechnical Institute (NGI) type (Bjerrum, L., and Landva, A., "Direct Simple Shear Tests on a Norwegian Quick Clay," Geotechnique, Vol. 16, No. 1, 1966, pp. 1–20 and Kjellman, W., "Testing the Shear Strength of Clays in Sweden," Geotechnique, Vol. 2, No. 3, pp. 225–232) and the Cambridge University (CU) type (Roscoe, K. H., "An Apparatus for the Application of Simple Shear to Soil Samples," Proc. 3rd ICSMFE, Vol. 1, 1953, pp. 186–191). Although both of these devices are unable to subject the sample to uniform states of stress and strain, there are important differences between them. One difference is the result of the geometry of the sample. Another difference is the measuring and determination of the stresses.

The NGI type accepts a cylindrical sample enclosed by a wire reinforced rubber membrane. The simplicity and ease with which field cores may be mounted in the NGI apparatus has made this model popular. In this device, however, only average shear and vertical stresses on the horizontal boundary can be determined. Some effort was directed to measuring the lateral stresses by using part of the wire reinforcement as a strain gage. However, it was found that the radial stresses were being measured. The radial stresses are neither equal to the lateral stress parallel to the direction of shearing nor the intermediate principal stress for simple shear stress state. Thus, it is not possible to use the measurements made in the NGI apparatus to compute the stress invariants which are necessary, at least, for the validation of mathematical models and for comparing the results of simple shear tests with other devices such as the triaxial device. The triaxial device is another common device for performing laboratory tests to study the stress-strain behavior of soils.

The CU type subjects a cuboidal sample to simple shear deformations imposed through the rotation of two hinged end flaps. The sample is surrounded by rigid boundaries and an array of load cells capable of measuring the normal and shear loads. From these measurements, the complete simple shear stress state of a mid-region of the sample can be computed. The CU apparatus has been used, largely in testing dry sands. The mounting and testing of clay samples in the device is very difficult. The area where the sample must be inserted must be dismantled before the sample is inserted and then reassembled. In addition, when a single series of clay tests was performed with a special version, the intermediate principal stress was not measured. The structure of the hinged end flaps also permits the seepage of water from the sample area leading to inaccurate measurements. Therefore, the routine testing of clays with this device is not feasible.

A common problem of many simple shear devices is the nonuniformity of stress/strain distribution within the soil specimen. A limiting factor in making measurements on soil samples has been the influence of the boundaries of the apparatuses, not found in the soil element in the field, on stress/strain distribution. This problem has been addressed in the past by the development of large-scale simple shear devices to overcome boundary influence. In addition, available devices could not identify and separately measure the lateral stresses $\sigma_x$ and $\sigma_z$.

The present invention is suitable for routine testing of earthen materials including clays and sands, as well as powders. This device provides sufficient measurements from which the complete stress and strain states including the lateral stresses $\sigma_x$ and $\sigma_z$ can be determined. Although this device does not eliminate the nonuniformities, the instruments are located in a region of the sample where uniform conditions are likely to prevail so as to circumvent the non-uniformities which are known to be predominant at the ends of the samples.

SUMMARY OF THE INVENTION

The present invention comprises a simple shear device for testing earthen samples and powders, which is capable of measuring a complete set of stresses during simple shear deformation. This device tests a cuboidal sample whose lateral sides are surrounded by a rubber membrane reinforced by a stack of plates. These plates are slidably movable laterally relative to one another.

The invention further comprises means of applying various loads and means for monitoring the results.

More particularly, the invention comprises a simple shear device and method for its use to test stress and strain characteristics of geologic and mineralogic particulate materials. The shear device particularly comprises:

(a) a cuboidal sample containing means comprising a stacked plurality of plates which are slidably movable laterally relative to one another, which plates have a hollow central area for holding the sample;

(b) spaced first and second platens having faces at between parallel and 45° relative orientation to one another, between which the plurality of plates containing the sample may be placed;

(c) means for applying a first force to said first platen urging it toward the second platen to compress said sample therebetween by means of said first force;

(d) means for applying a second force to one of said platens to urge said platen in an angular direction relative to the direction of said first force to apply a shear force to the sample;

(e) means for monitoring the resulting stresses and strains in said sample when said forces are applied to said sample while confined between said platens.

DETAILED DESCRIPTION OF INVENTION

The present invention generally comprises a simple shear device for measuring a complete set of stresses, during simple shear deformation of earthen samples and powders. The complete set of stresses includes the normal and shear stresses as well as the lateral stresses and the porewater pressure. More particularly, the present invention comprises a cuboidal sample whose lateral sides are surrounded by a rubber membrane reinforced by a stack of plates. These plates are slidably movable laterally relative to one another.

The invention also comprises means for applying various loads and means for monitoring the results. One of the plates may be used as a load transducer to determine the lateral stresses on planes normal and parallel to the direction of shearing. A load cell located around the middle of the lower central section of a top platen provides data to deduce the normal and shear stresses as well as porewater pressure in the central section of the sample. Therefore, frictional corrections and stress concentration effects are eliminated.

The plate being used as a load transducer provides measurement of the lateral stresses $\sigma_x$ and $\sigma_z$. In the available devices the lateral stresses $\sigma_x$ and $\sigma_z$ cannot be identified and measured separately. Therefore, in the present invention a complete set of stresses necessary for simple shear tests can be made.

The following is a list of definitions for terms used in connection with the present invention:

Stress—stress at any point in a body is the internal force acting on a unit area at that point.

Normal Stress—this is the force acting perpendicular to the unit area.

Shear Stress—the force acting parallel to the unit area.

Strain—strain measures the deformation of the body due to the applied stress.

Normal Strain—with specific reference to the present invention means the vertical deformation of the sample.

Shear Strain—is the change in the angle between two straight lines drawn inside the body that were perpendicular before deformation.

Shear—is a straining action wherein tangentially applied forces produce a sliding or skewing type of deformation.

Load cell—is a unit capable of measuring several forces and/or several stresses.

Principal stresses—are the normal stresses on a plane in the absence of shear stresses.

Transducer—A device which converts energy from one form to another. As used herein the transducer converts energies resulting from forces and movements, e.g., from stresses and strains, to electrical signals representing such forces and movements. A contact transducer is one which is in the direct contact with the material.

The following description of the device and operation of the device are not intended to be limiting in any manner, they are merely illustrative. Various modifications, applications and changes may occur to those skilled in the art without departing from the true spirit and scope of the invention.

Figure 1:
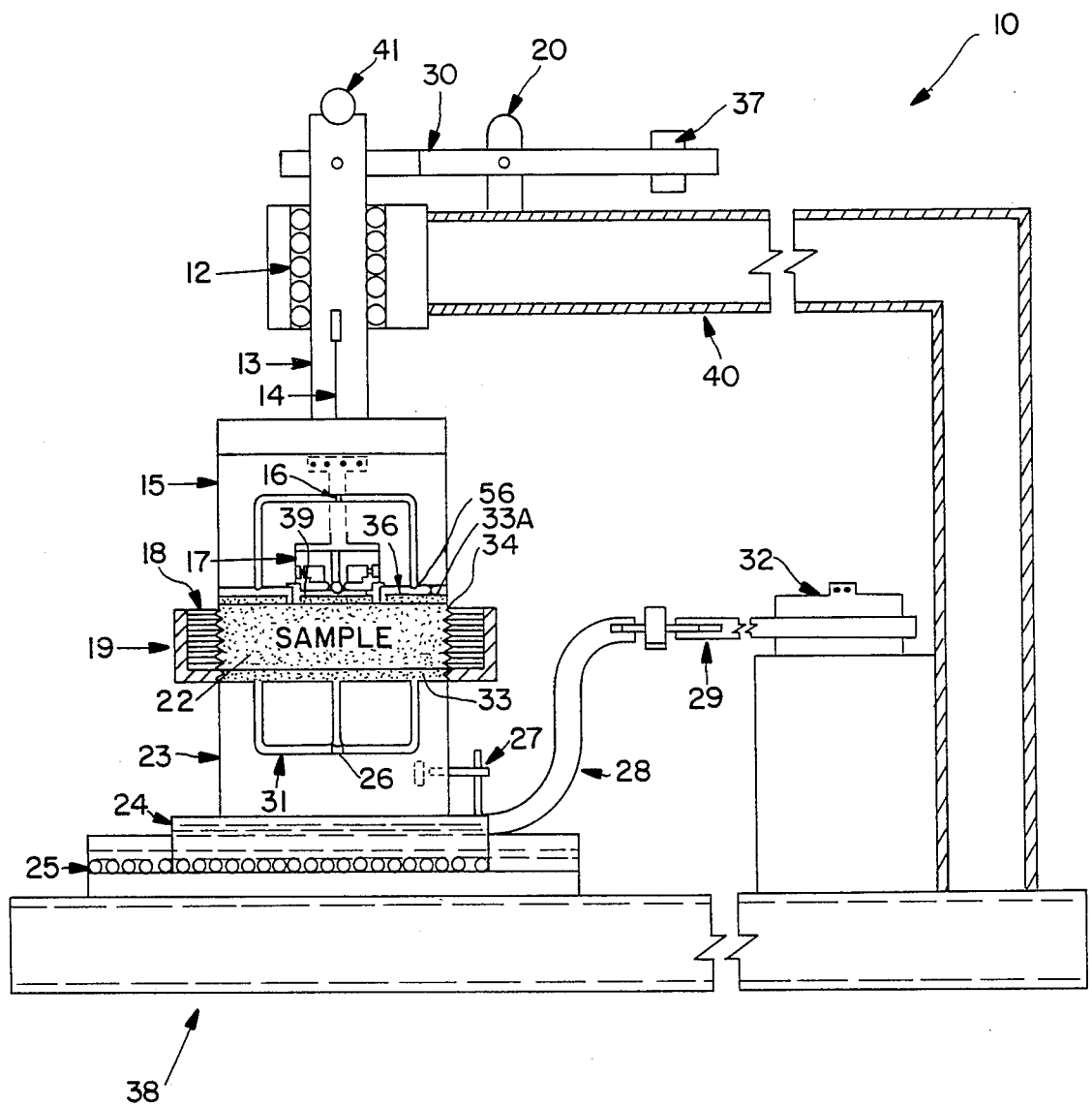
FIG. 1 is a cross-sectional plan view of the simple shear device of this invention.

As seen in FIG. 1, the apparatus of the present invention (10) tests a cuboidal sample (22) whose sides are enclosed by a stack of plates (18) which sample sides are also desirably enclosed by a first rubber membrane (34) reinforced by the plates. "Cuboidal" is broadly used herein and means a prism (desirably a rectangular prism) having rectangular (usually square) base faces. Although plates made of various materials and various sizes are within the scope of the invention, in a preferred embodiment the plates are Teflon (trademark for polytetrafluoroethylene coated) thin aluminum plates. A preferred size of the plates are 80.6 mm × 80.6 mm × 1 mm thick, having an opening centrally located within the plates. The size of the opening is 70.6 mm × 70.6 mm × 1 mm thick, thus a border of 10 mm width and 1 mm thickness surrounds the opening. When the plates are stacked such that the openings are in vertical alignment, a cuboidal opening is formed in the center to receive the sample. Other sizes may be used in accordance with the present invention.

The rubber membrane (34) may be about 0.3 mm thick. Other sizes are within the scope of this invention. The top and bottom faces of the sample (22) are held between two platens (15,23). "Platen" as used herein means a jaw having a surface for contacting and gripping a sample which jaw has appropriate recesses for containing sensing devices and auxiliary apparatus. The bottom platen (23) is fixed to a trolley (24) running on a horizontal roller bearing block (25) to reduce friction. The trolley (24) in turn is connected to the shaft (29) of a servo hydraulic actuator assembly (32) through a shear arm (28). Any one of a variety of servo-hydraulic actuators or pneumatic actuators or other drivers well known in the art, may be used. Other devices which are able to apply loads may also be used.

A rough porous plastic plate (33) is recessed into the bottom platen (23) to provide a rough interface between the sample (22) and the bottom platen (23) and for drainage of porewater, through drainage channels (31).

The top platen (15) houses a centrally located load cell (17) which can measure the vertical and shear loads as well as the porewater pressure. Porous plastic plate (33A) is recessed in the face (35) (FIG. 3) of the load cell (17) and on the platen cap (36) (FIG. 1) for purposes mentioned above. In addition, plate (33A) acts to transmit forces from pressure blocks (55A) to sample (22).

The top platen (15) is connected to a square shaft (13) which moves through a vertically mounted bearing block (12) to reduce friction. The bearing block (12) is attached to an arm (40) of the device of the present invention (10). The shaft (13) is pivotally mounted to a first end of a rod (30). The center of the rod (30) is pivotally mounted to a fulcrum (20). The fulcrum (20) is fixed to the arm (40). A counterbalance (37) is slidably mounted on a second end of rod (30). Two Linear Variable Differential Transducers (14 and 27) are placed on the device of the present invention which are capable of measuring the vertical and horizontal displacements. A first Linear Variable Differential Transducer (LVDT) (14) may be placed parallel to the square shaft (13) and measures the vertical displacement. A second LVDT (27) may impinge on the bottom platen (23) and is fixed to base (38) and measures the horizontal displacement.

Shear displacement/shear load is applied through a closed loop servo-hydraulic actuator (32) which is controlled either manually or by a computer. Upon application of various loads, the stacked plurality of plates are slidably movable laterally relative to one another such that not only compression but deformation of the sample can occur. Therefore, the cuboidal sample is allowed to transform into a parallelogram type shape which closely simulates simple shear deformation. Vertical load can be applied either through dead load or by a bellofram (pneumatic pressure) unit or any similar means through ball bearing (41).

SAMPLE PREPARATION

Before sample preparation begins, one end of first rubber membrane (34) is slipped on to the bottom platen (23) and the thin plates (18) are stacked in a mold (19) and then placed over the first rubber membrane (34). The mold (19) is essentially used to mold the thin plates (18) in vertical alignment. The mold (19) may be made of a variety of materials and may be any plastic or metal which may be used in accordance with the present invention. The other end of the first rubber membrane (34) was turned over the sides of the mold (19). Insertion of the mold (19) which contains; the first rubber membrane (34); and the thin plates (18), is made between the top and bottom platens (15,23). The mold (19) will be removed prior to testing, and the rubber membrane (34) will be allowed to overlap onto the top platen (15). The height of the samples can vary depending on the size of the sample desired. A preferred range of the sample height is from about 1-30 mm.

The sample may be loose or consolidated. For purposes of illustration, loose sand samples were prepared by raining the dry material through a hopper with intervening meshes. Various hoppers may be utilized, similar to the hopper disclosed by Cole (The Behavior of Soils in Simple Shear Apparatus, Ph.D. Thesis, Cambridge University, U.K. 1967). The size of the aperture of the hopper pouring mechanism can be adjusted so that samples of various initial void ratio could be repeatedly poured in the apparatus.

The sand samples were normally poured to a height of 23 mm. An acrylic plate was thinly smeared with silicone grease and lowered to contact the sand surface. The sand trapped by the greased plate was removed and the process repeated until the height attained was 20 mm. The thickness of the acrylic plate was designed with a step so that when the surface of the step rests evenly on the mold the height of sample achieved is then 20 mm. This procedure provides a level surface without causing any significant change in void ratio at the top of the sample. The top platen was then lowered to the prepared said surface, the mold was released and vertical loads were imposed. Subsequently, shear displacements were applied at a constant rate.

In the case of clays, reconstituted samples were poured in the membrane and then consolidated. For field cores or artificially consolidated clays a square cutter of internal dimensions 70 mm×70 mm×20 mm was constructed to obtain the required sample size. The square cutter is designed to fit over the mold so that samples from field cores could be pushed through the cutter into the rubber membrane with the thin plates in place. Saturation of the clay sample to remove air voids was achieved by back pressure saturation through valves (16 and 26).

MEASUREMENT OF STRESSES AND STRAINS

Figure 2:
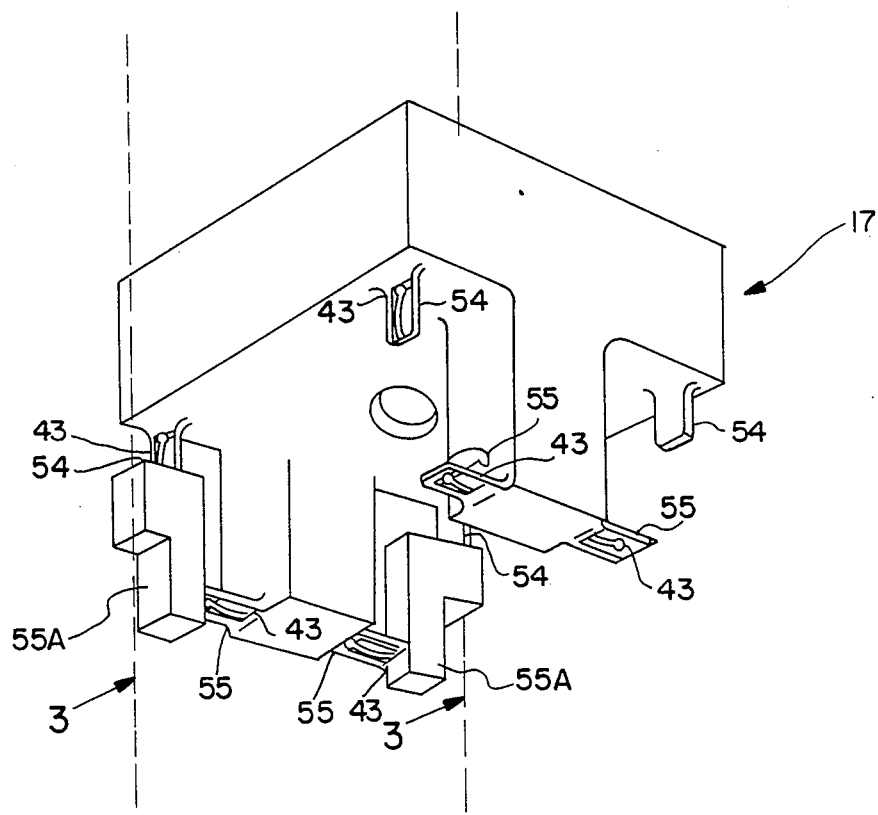
FIG. 2 is a perspective view of a load cell 17 as shown in FIG. 1 with two of the four pressure blocks 55A cut away for enhanced viewing.

The shear and vertical stresses and the porewater pressures on an area 25 mm×25 mm at the center of the sample (22) (sample core) are deduced from a single load cell (17). A 25×25 mm area was selected as the area for which stress and strain measurements are made. It is to be understood, however, that any measurement area may be arbitrarily selected. The load cell (FIG. 2) in a preferred embodiment, comprises four pressure blocks (55A) which transmit forces to sample (22) through plastic plate (33A). Four thin vertical columns (54) and four thin beams (55) are also provided. The four pressure blocks (55A) are each supported by a column (54) and a beam (55). A strain gage (43) is attached to each column (54) and each beam (55) and wired into two Wheatstone bridges (not shown). Other devices may also be used to measure resistance and are within the scope of this invention. The circuits are such that the vertical columns (54) are only sensitive to vertical loads and the beams (55) to horizontal loads. A variety of wiring schemes could be conceived which will allow the measurement of the eccentricity of the vertical load, and/or the eccentricity of the shear load. These schemes were not implemented because the load cell is located at the center of sample where the eccentricities of loads are likely to be small or negligible. The whole load cell (17) assembly was coated with water protection compounds. The load cell (17) can be designed for any stress level. One example is a maximum working stress of 1500 kN/m² (kN=kilonewtons, m=meter).

Figure 3:
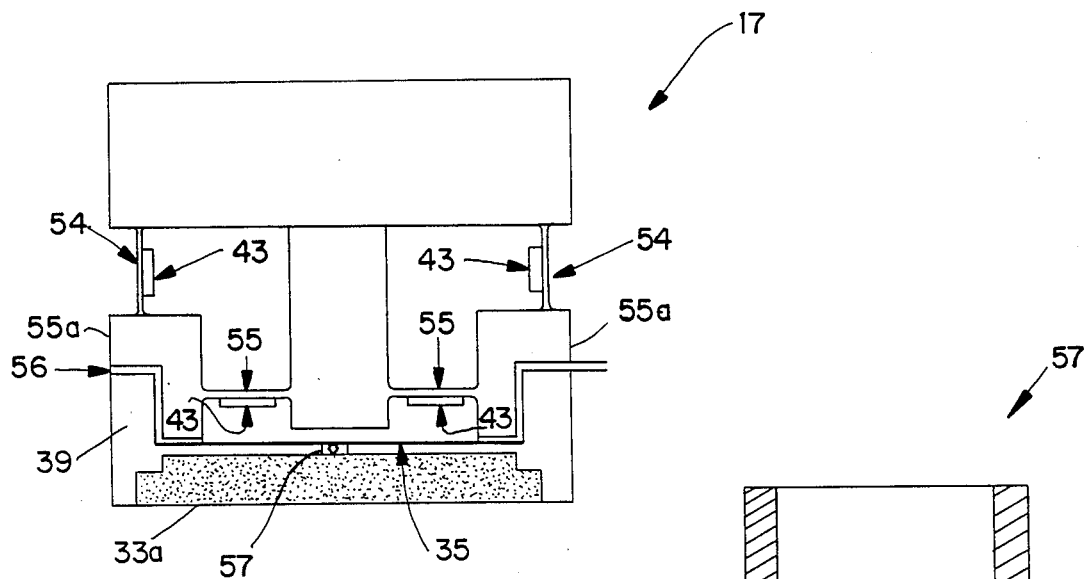
FIG. 3 is a cross-sectional view along line 3—3 of a load cell as shown in FIG. 2.

A metal cap (39) to cap the face (35) of the load cell (17) and to connect the prewater pressure transducer (57) is made from any metal plate (FIG. 3). A second rubber membrane (56) is placed between the load cell (17) and the metal cap (39) and continues between the top platen (15) and its cap (36). This membrane (56) is intended to prevent penetration of fluid into the load cell (17).

Figure 4:
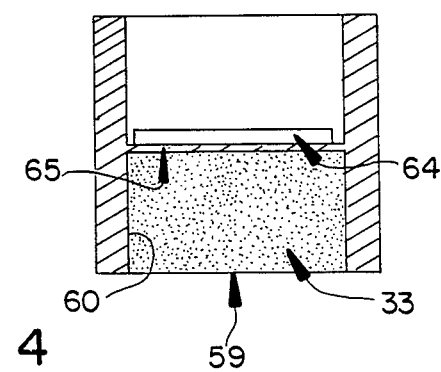
FIG. 4 is a cross-sectional magnified view of the porous tip 57 of the load cell as shown in FIG. 3.

A porewater pressure transducer (57) (FIG. 4) was designed with a recess (60) in which a porous plastic was inserted to form a porous tip (59) to measure the porewater pressure. This transducer is firmly attached to the load cell cap (39) and requires no deairing. A diaphragm strain gauge (64) is attached to the diaphragm (65) of the porewater pressure transducer (57).

The porewater pressure transducer (FIG. 4) was calibrated separately by applying increasing/decreasing water pressure and noting the change in voltage from a Wheatstone bridge circuit (not shown). The load cell (17) was mounted into the top platen (15) and calibrated by independently applying increasing/decreasing vertical and horizontal loads. A gap 0.05 mm between the load cell cap (39) and the top platen (15) was filled in with silicone rubber before calibration began.

Figure 5:
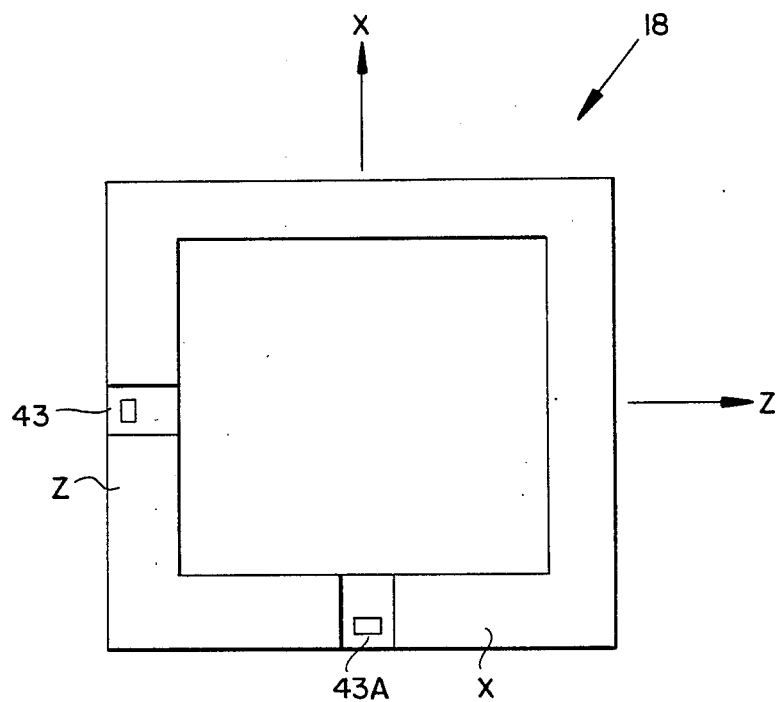
FIG. 5 is a top plan view of a lateral stress transducer 18 as shown in FIG. 1.

One of the thin aluminum plates (18) was converted to a lateral stress transducer (FIG. 5). This was done by reducing the thickness at the center of two adjacent sides and attaching strain gages (43 and 43A) on both the top and bottom faces. The strain gages (43 and 43A) were wired into two Wheatstone bridges (not shown) such that each circuit is only sensitive to axial strains. These strain gauges were calibrated by incrementally applying equal stresses to the sides x (FIG. 5) and noting the voltage outputs from gauges (43 and 43A). The stresses are then applied to the sides z and again the voltage outputs from gauges (43 and 43A) are recorded. Four slope constants ($a_{xx}$, $a_{zx}$, $a_{zz}$ and $a_{xz}$) for the stress-voltage relationship are obtained through this calibration procedure. The lateral stresses $\sigma_x$ and $\sigma_z(=\sigma_2)$ were obtained by solving two simultaneous equations, $$\begin{Bmatrix} \sigma_x \\ \sigma_z \end{Bmatrix} = \begin{bmatrix} a_{xx} & a_{xz} \\ a_{zx} & a_{zz} \end{bmatrix}^{-1} \begin{Bmatrix} V_x \\ V_z \end{Bmatrix}$$

where $V_x$ and $V_z$ are the change in voltage in the circuits for the side x and side z respectively.

The vertical and horizontal displacements were measured by the two LVDT (Linear Variable Differential Transducer) (14 and 27). The vertical displacement is measured by a first LVDT (14) and the horizontal displacement is measured by a second LVDT (27). Similar measuring instruments may also be used.

COMPUTATION OF STRAINS AND STRESSES

From measurements of the vertical and horizontal displacements, the vertical strains ($\epsilon_y$) and shear distortion ($\alpha$) were computed: Thus, $$\epsilon_y = \Sigma \dot{\epsilon}_y = \Sigma - y/h$$

$$\alpha = \Sigma \dot{\alpha} = \dot{x}/h$$

where y and x are the horizontal and vertical displacements, h the current height of the sample, and the superimposed dot denotes an increment. Mohr's circle of strain can be drawn and the principal strains and their directions determined. Thus the following calculations can be made:

(1) the volumetric strain $$\epsilon_v = \epsilon_1 + \epsilon_3$$

(2) the shear strain $$\gamma = \epsilon_1 - \epsilon_3$$

(3) the angle of inclination ($\xi$) of the major principal strain increment to the vertical plane;

where $\epsilon_1$ and $\epsilon_3$ are the major and minor principal strains, and can be determined from Mohr's circle of strain. Mohr's circle of strain is a convenient graphical representation used to represent the state of strain in a material. A more detailed definition can be found in Introduction to Solid Mechanics, by I.H. Shames, Prentice Hall, Inc., 1975, p. 317 et seq. which is being incorporated by reference herein.

Figures 6A, 6B:
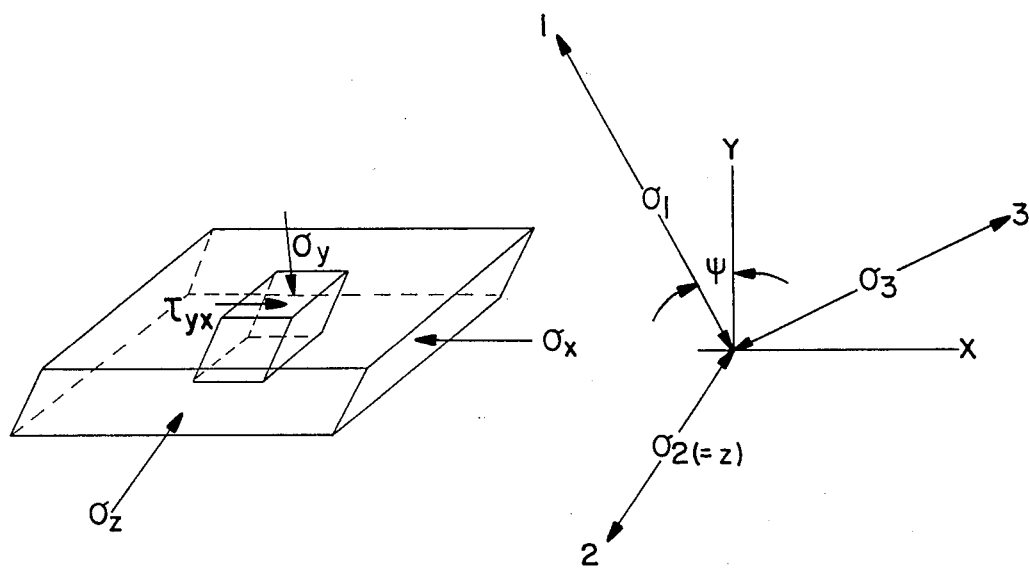
FIG. 6A is a representation of the measured stresses [(a) measured (b) deduced] for the sample core in the present simple shear device.
FIG. 6B is a representation of the deduced stresses for the sample core in the present simple shear device.

The stresses which are measured by this new simple shear apparatus are shown in FIG. 6a where $\sigma_y$=vertical stress; $\tau_{yx}$=shear stress on the horizontal plane; $\sigma_x$=the normal stress on the plane perpendicular to the plane of shearing; $\sigma_z$=normal stress on the plane parallel to the plane of shearing. The following assumptions are made in the computation of the stress state of the sample.

(1) a mid-region of the sample—the sample core—approximately 25 mm×25 mm×20 mm will be under a uniform simple shear stress state. Thus, the shear stress on the vertical sides of the sample core is equal but of opposite direction to $\tau_{yx}$. This assumption is not unreasonable since in tests in other simple shear devices it was shown that indeed the middle of the sample will be under uniform simple shear conditions. Numerical analyses also support the assumption made here.

(2) The lateral stresses $\sigma_x$ and $\sigma_z$ measured at the mid-height on the boundaries are representative of those acting on the vertical sides of the sample core.

With these assumptions, the principal stresses which are computed for the sample core are shown in FIG. 6b. In this figure $\sigma_1$ and $\sigma_3$ are the major and minor principal stresses, $\sigma_2 = \sigma_z$ and $\Psi$ is the inclination of the principal stress to the vertical plane. The inclination of the principal stress increment to the vertical is also computed. The stress invariants p and q are:

$$p = \frac{\sigma_1 + \sigma_2 + \sigma_3}{3}$$

$$q = \frac{1}{2}[(\sigma_1 - \sigma_2)^2 + (\sigma_2 - \sigma_3)^2 + (\sigma_3 - \sigma_1)^2]^{\frac{1}{2}}$$

If a computer is used, all these calculations are carried out on-line during the tests so that one can keep track of the test as well as send control signals if desired.

TEST RESULTS

Tests on Ottawa (American Society for Testing and Materials (ASTM), C-109) sand and a Kaolin clay from Georgia Kaolin Company, Inc. are reported here. The test results are intended to illustrate some of the main advantages of this new simple shear apparatus. The Ottawa sand has a mean diameter of 0.36 mm, specific gravity of 2.65 $e_{max}=0.80$ and $e_{min}=0.50$. e is defined as the void ratio, i.e., volume of void spaces relative to the solids in the material. $e_{max}$ is the maximum void ratio. $e_{min}$ is the minimum void ratio. The Kaolin clay has a liquid limit of 55% and plasticity index of 24%.

The Ottawa sand was tested in a dry condition under a constant vertical load. This type of test will be referred to as a drained test. The Kaolin clay was thoroughly mixed with water to form a slurry whose water content was twice the liquid limit. The slurry was poured into the simple shear device and one dimensionally consolidated up to a vertical effective stress of 140 kPa (kilopascal) under a back pressure of 30 kPa. After consolidation was completed (that is, when the excess porewater pressure becomes less than 1% of its initial value) the sample was sheared under constant volume. This was accomplished by locking in position the vertical shaft, thus preventing any vertical movement of the top platen. Six tests were conducted on Ottawa sand—four at relative densities ($D_r$) ranging between 19 and 25% (called series A here) and two at an average relative density of 38% (called series B).

STRESS-STRAIN RESPONSE

Figure 7A:
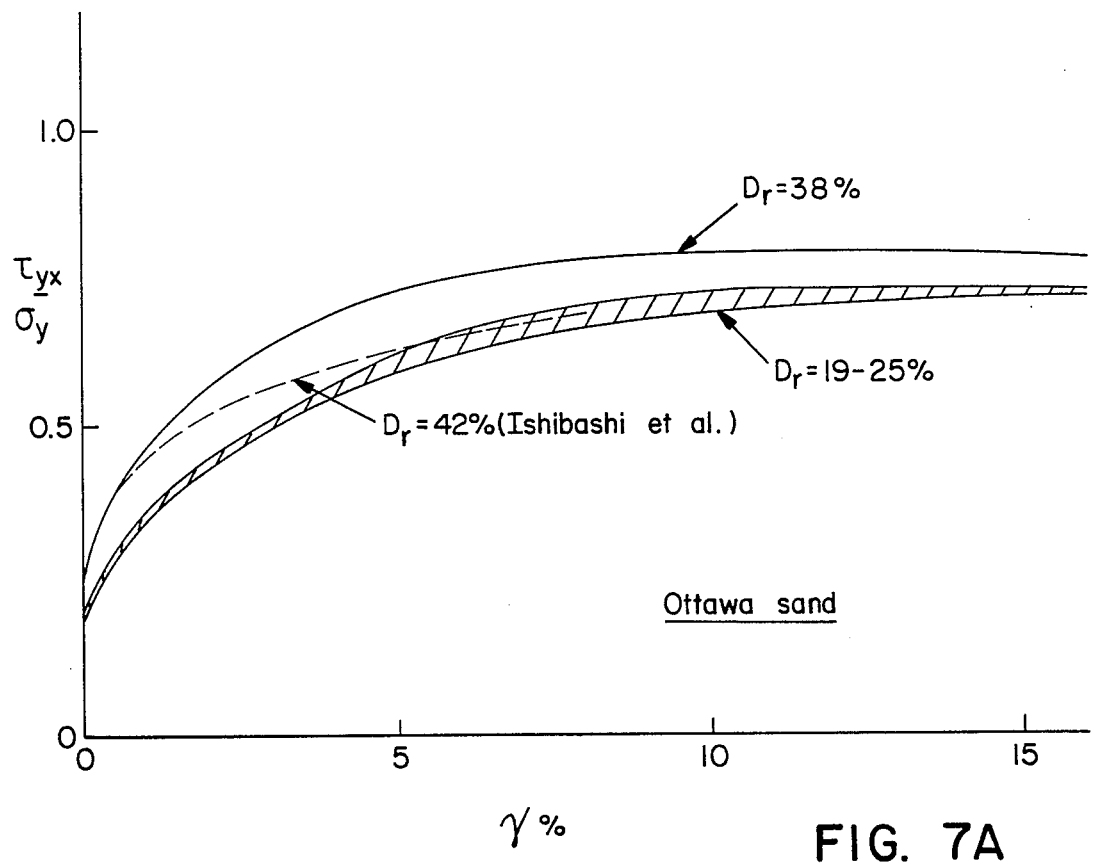
FIGS. 7A and 7B illustrate the stress-strain response for Ottawa C109 sand.
Figure 7B:
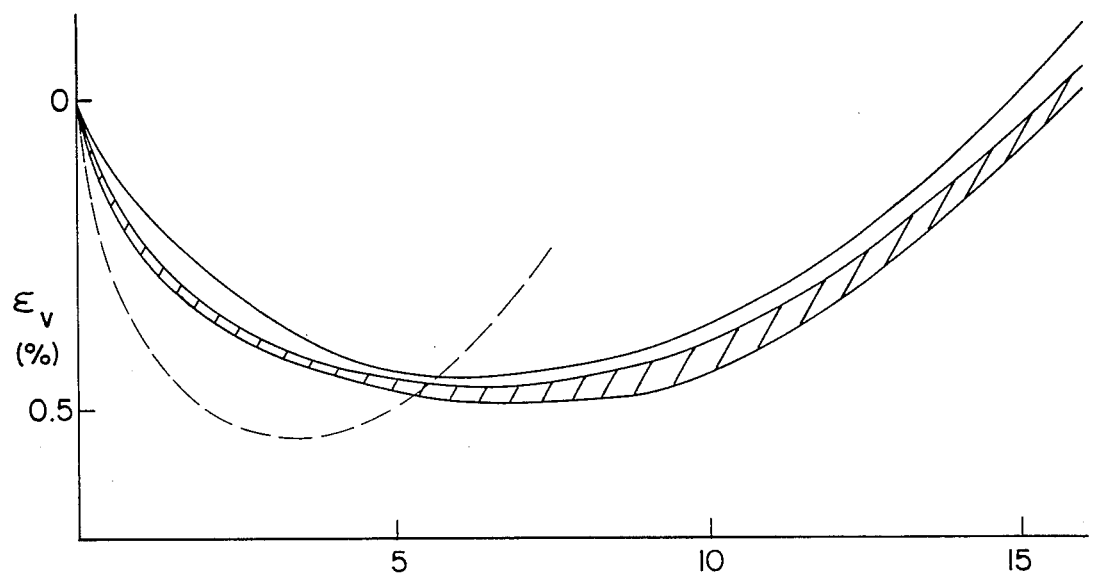

FIGS. 7A and 7B show the stress-strain response of Ottawa (ASTM C-109) sand. The spread of the results of series A is shown by the hatched lines. The results of the same sand tested at a $D_r$ of 42% in the hollow cylinder device by Ishibashi (Ishibashi, M., Kawamura, M. and Bhatia, S. K., "Effect of Initial Shear on Cyclic Behavior of Sand," Journal of Geotechnical Engineering, Vol. 11, No. 12, 1985, pp. 1395–1410), are superimposed in FIG. 7a. The stress strain response up to 15% shear strain between the hollow cylinder apparatus (HCA) results and those of the present invention for roughly the same relative density (42% and 38% respectively) are in very good agreement. HCA is a device which applies controlled rotation to a hollow cylindrical sample. Beyond a shear strain of 1%, the simple shear device of the present invention (Budhu device) generates a higher shear stress ratio ($\tau_{yx}/\sigma_y$) than the results reported by Ishibashi et al. The maximum difference in shear stress ratio is about 15 percent. A greater difference between HCA and Budhu device results are depicted in the volumetric strain-shear strain response (FIG. 7b). The HCA results showed a maximum compression to occur at a shear strain of about 3% compared with 7% for the Budhu device. The volumetric strains obtained from the Budhu device were corrected for compression of the apparatus and no account was taken for compression of the rubber membrane laterally. It is presumed that this latter effect is not very significant.

Figure 8:
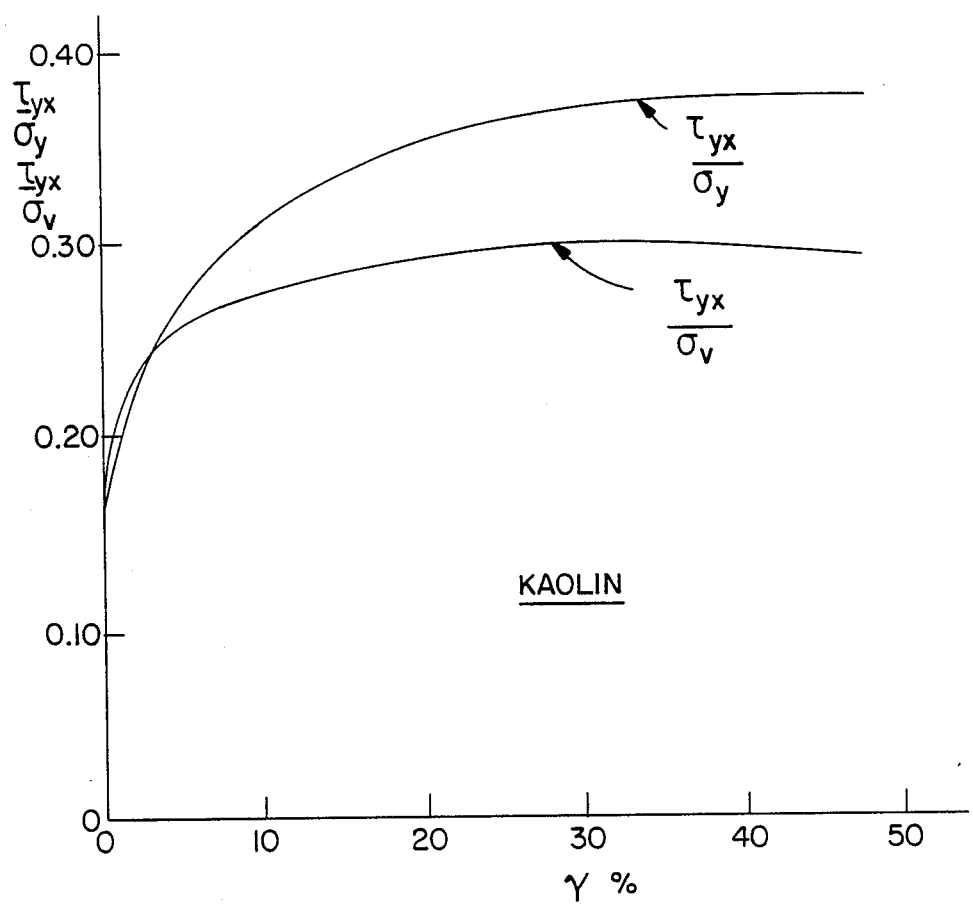
FIG. 8 illustrates the stress-strain response of Kaolin.

FIG. 8 shows the stress-strain response of the Kaolin clay sheared at constant volume. The shear stresses are normalized with respect to the vertical effective stress on the sample core $o_y$ and to the average applied vertical pressure $\sigma_y$. The maximum values attained are: $\tau_{yx}/\sigma_y=0.36(\phi=19.8°)$ at about 35% shear strain and $\tau_{yx}/\sigma_v=0.29$ at about 25% shear strain, ($\phi=\tan^{-1}[\tau_{yx}/\sigma_y]$). Airey (Airey, D. W., "Clays in Circular Simple Shear Apparatus," Ph.D. Thesis, Cambridge University, U.K., 1984) using a specially designed NGI type simple shear device reported values of $\tau_{yx}/\sigma_y=0.44$ at a shear strain of 22% and $\tau_{yx}/\sigma_v=0.18$ at a shear strain of 11% for normally consolidated speswhite Kaolin (liquid limit=69%, plasticity index=31%).

Figure 9:
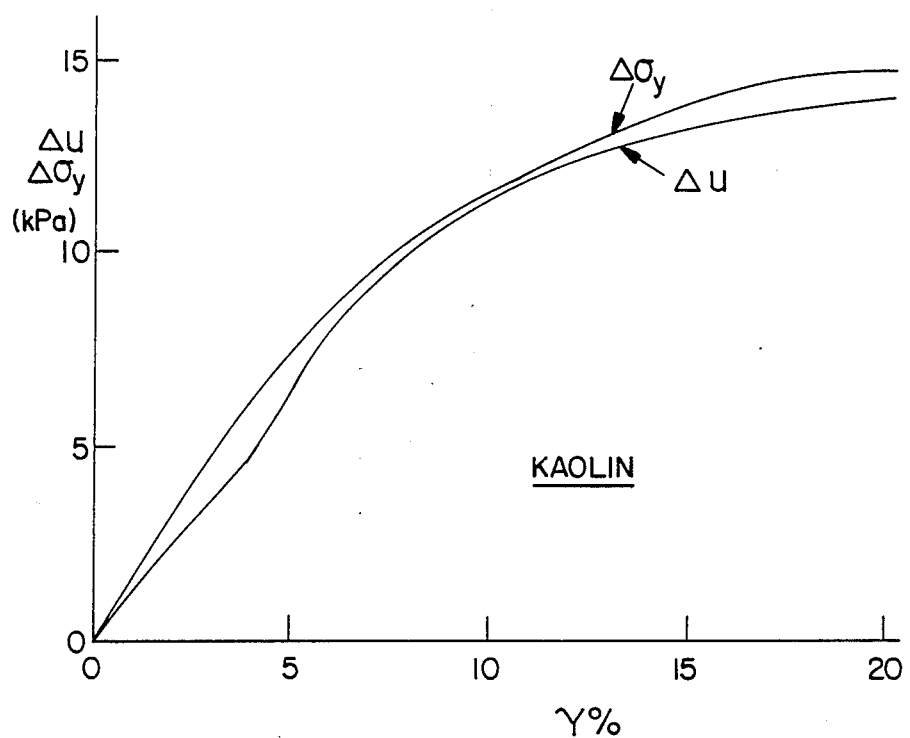
FIG. 9 illustrates the development of excess porewater pressures and change in vertical effective stress for constant volume test.

In the NGI type device, the constant volume test is usually conducted under drained conditions and the average vertical stress is adjusted to maintain a constant height during shear. The change in vertical stress is then assumed to be equal to the change in porewater pressure which would occur under undrained conditions. This assumption is controversial among some researchers. FIG. 9, using the cell of the present invention, shows a comparison between the excess porewater pressure ($\Delta u$) measured by the porewater pressure sensing element (transducer [57]) in the load cell located at the sample core and the vertical effective stress ($\Delta \sigma_y$) measured by the same load cell for the test on Kaolin clay against shear strain. During the test no drainage of porewater was permitted. There are some differences between the results. But, it appears, for practical purposes, that it is acceptable to take $\Delta u = \Delta \sigma_y$. However, it is uncertain whether this is valid for the general test situation in the NGI type devices where average stresses are measured.

STRESS PATH

The stress paths using stress invariants cannot be obtained from current simple shear devices except the Cambridge University's device. Thus, the comparison of results between different testing devices, the validation of constitutive models and certain principles in soil mechanics have to be carried out under restricted circumstances using normalized stress ratios $\tau_{yx}/\sigma_v$.

Figure 10:
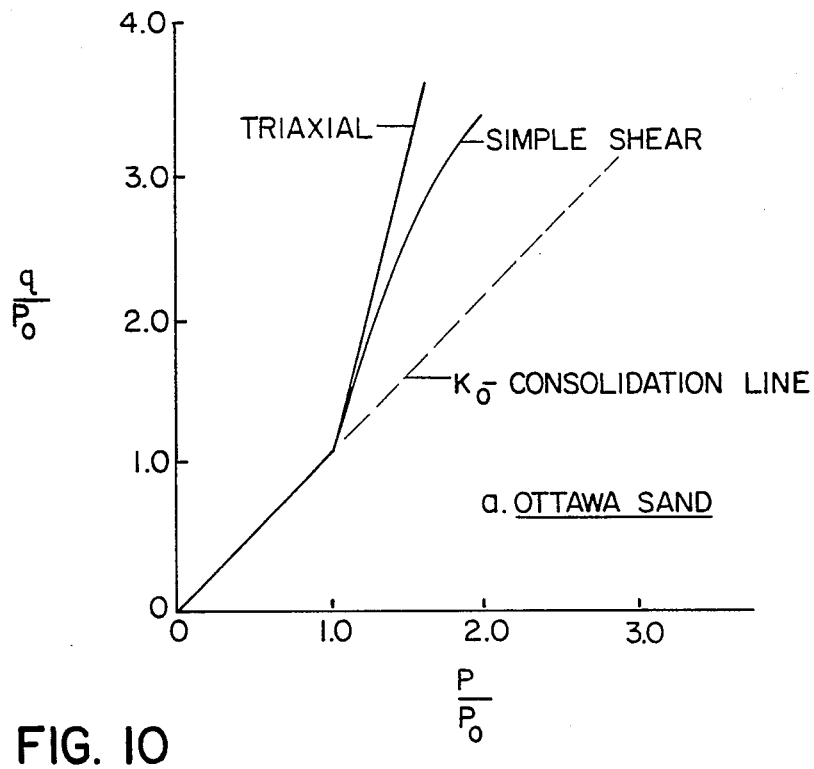
FIG. 10 illustrates the stress paths for Ottawa sand and Kaolin.

FIG. 10 shows the effective stress path in ($p/p_o$, $q/p_o$) space where $p_o$ is the initial mean effective stress for Ottawa sand. The effective stress path for a one dimensionally ($K_o$) consolidated conventional prior art triaxial drained test is superimposed in FIG. 10. These effective stress paths are significantly different so that the stress-strain response of this sand would be different when tested under simple shear and triaxial conditions. One could, by suitable adjustment of the axial and radial stresses, follow, in the triaxial device, an effective stress path similar to the simple shear effective stress path shown in FIG. 10. However, the sample should not be expected to respond in the same manner as if subjected to simple shear conditions since the rotation of principal axes in the latter test may have a profound effect on the behavior of the sample.

Figure 11:
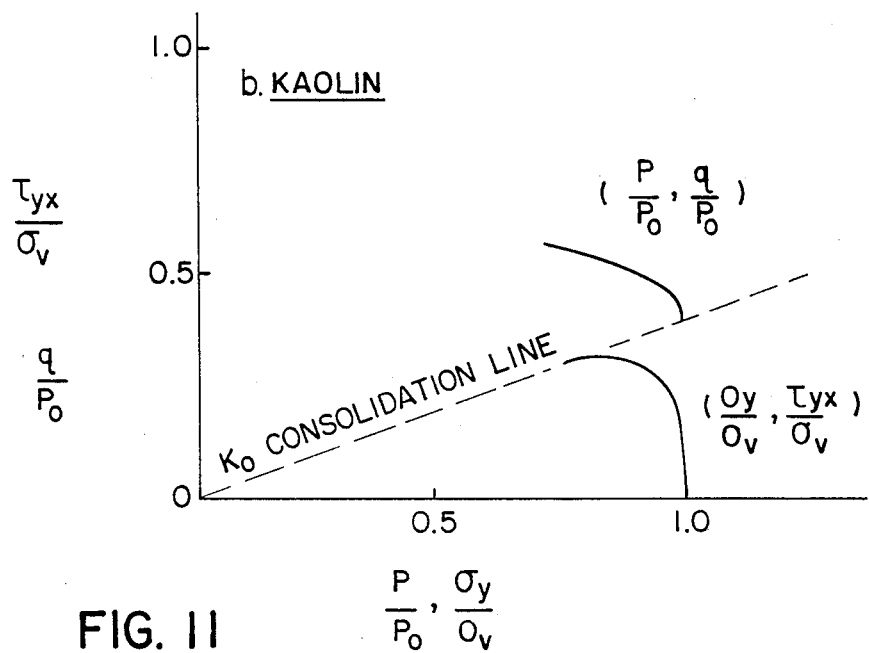
FIG. 11 illustrates the stress paths for Kaolin.

FIG. 11 depicts the effective stress paths in ($\sigma_y/\sigma_v$, $\tau_{yx}/\sigma_v$) and ($p/p_o$, $q/p_o$) spaces for the Kaolin clay. Since in simple shear tests, the sample is usually one-dimensionally consolidated prior to shearing, an initial deviatoric stress $q_o=\sigma_y(1-K_o)$ where $K_o$ is lateral earth passive coefficient at rest is imparted to the sample. Thus, the effective stress paths in ($p/p_o$, $q/q_o$) space start on the one dimensionally consolidation line at the commencement of shearing. The differences in effective stress paths shown in FIG. 11 is a result of changes in the lateral stresses $\sigma_x$ and $\sigma_2$ during simple shear deformation.

The above description of the device and operation of the device are not intended to be limiting in any manner, they are merely illustrative. Various modifications, applications and changes may occur to those skilled in the art without departing from the true spirit and scope of the invention.

What is claimed is:

1. A simple shear device for testing earthen samples and powders comprising:

(a) a cuboidal sample containing means comprising a stacked plurality of plates which are slidably movable laterally relative to one another, which plates have a hollow cuboidal central area for holding the sample;

(b) spaced first and second platens having faces at between parallel and 45° relative orientation to one another, between which the plurality of plates containing the sample may be placed;

(c) means for applying a first force to said first platen urging it toward the second platen to compress said sample therebetween by means of said first force;

(d) means for applying a second force to one of said platens to urge said platen in an angular direction relative to the direction of said first force to apply a shear force to the sample;

(e) means for monitoring the resulting stresses and strains in a central section of said sample when said forces are applied to said sample while confined between said platens.

2. A simple shear device for testing earthen samples and powders comprising:

(a) a cuboidal sample containing means comprising a rubber membrane reinforced by a stacked plurality of plates which are slidably movable laterally relative to one another and have a hollow cuboidal central area for holding the sample;

(b) spaced lower and upper platens parallel to one another between which the plurality of plates containing the sample may be placed;

(c) means for applying a vertical load to said upper platen urging it toward the lower platen to compress said specimen therebetween;

(d) means for applying a shear load or shear displacement to the lower platen;

(e) means for monitoring the resulting stresses and strains in a central section of said sample, when force is applied to said sample while confined between said platens.

3. The device of claim 2, wherein the plurality of plates are placed over said rubber membrane.

4. The device of claim 2, wherein the stacked plates are aluminum plates.

5. The device of claim 4, wherein the aluminum plates are coated with polytetrafluoroethylene.

6. The device of claim 2, wherein the means for applying a vertical load is by a dead load.

7. The device of claim 2 wherein the means for applying a shear load or shear displacement is by a servo-hydraulic actuator.

8. The device of claim 2, wherein the means for monitoring comprises at least one of a load cell, a load transducer, or a Linear Variable Differential Transducer.

9. The device of claim 8, wherein the load transducer is derived from one of the plates in the stacked plurality of plates.

10. The device of claim 9 wherein the load transducer derived from one of the plates in the stacked plurality of plates comprises a plurality of strain gauges which are capable of measuring lateral stresses on planes normal and parallel to the direction of shearing.

11. The device of claim 8 wherein the load cell is in the upper platen and comprises a pore water pressure transducer.

12. The device of claim 8 wherein the load cell is capable of measuring the normal and shear stresses as well as the porewater pressure in the central section of the sample.

13. The device of claim 8 wherein the Linear Variable Differential Transducer is capable of measuring vertical or horizontal displacements.

14. The device of claim 13 wherein the Linear Variable Differential Transducer is attached to the lower platen.

15. The device of claim 13 wherein the Linear Variable Differential Transducer is parallel to a square shaft, said square shaft being connected to said upper platen.

16. The device of claim 2 further comprising horizontal roller bearing means such that when shear load is applied, the lower platen may be laterally displaced.

17. The device of claim 2 further comprising vertical roller bearing means such that when a vertical load is applied, the upper platen may be vertically displaced.

18. The device of claim 2 wherein the upper and lower platens comprise liquid draining means.

19. The device of claim 18 wherein the liquid draining means comprises porous plastic contacting the sample such that draining of liquid from the sample is permitted.

20. The device of claim 19 further comprising drainage channels for the liquid.

21. A method for testing earthen materials and powders comprising the steps of:

(a) placing a cuboidal sample, between first and second platens having faces at between parallel and 45° relative orientation to one another, said sample being in a cuboidal sample containing means, which containing means comprises a stacked plurality of plates which are slidably movable laterally relative to one another and which plates have a hollow cuboidal, central area for holding the sample;

(b) applying a first force to said first platen urging it toward the second platen so that the sample is compressed therebetween by said first force;

(c) applying a second force to one of said platens to urge said platen in an angular direction relative to the direction of said first force, thus applying a shear force to said sample;

(d) monitoring the resulting stresses and strains in a central section of said sample when said forces are applied to said sample while confined between said platens.

22. A method for testing earthen materials and powders comprising the steps of:

(a) placing a cuboidal sample in a rubber membrane reinforced by a stacked plurality of plates in a mold between a lower and an upper platen, said stacked plurality of plates having a hollow cuboidal central area for holding the sample, and said lower and upper platen being parallel to one another;

(b) removing said mold;

(c) applying a vertical load to said upper platen;

(d) applying a shear load or shear displacement to said lower platen;

(e) monitoring the resulting stresses and strains in a central section of said sample.

23. The method of claim 22 wherein the result is monitored by at least one of a load cell, a load transducer, or a Linear Variable Differential Transducer.

24. The method of claim 23 wherein the load transducer comprises a plurality of strain gauges.

25. The method of claim 23 wherein the load cell comprises a pore water pressure transducer.

26. The method of claim 22 wherein a complete set of stresses is measured.

* * * * *